US012802276B2

(12) United States Patent
Walz et al.

(10) Patent No.: US 12,802,276 B2
(45) Date of Patent: Nov. 17, 2026

(54) METHOD FOR CALIBRATING A STEREOSCOPIC MEDICAL MICROSCOPE, AND MEDICAL MICROSCOPE ARRANGEMENT

(71) Applicant: Carl Zeiss Meditec AG, Jena (DE)

(72) Inventors: Felicia Walz, Schwäbisch Gmünd (DE); Dominik Scherer, Aalen (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/784,879

(22) Filed: Jul. 25, 2024

(65) Prior Publication Data

US 2024/0386609 A1 Nov. 21, 2024

Related U.S. Application Data

(63) Continuation of application No. PCT/EP2023/051629, filed on Jan. 24, 2023.

(30) Foreign Application Priority Data

Jan. 25, 2022 (DE) ..................... 10 2022 200 821.9

(51) Int. Cl.
*H04N 13/239* (2018.01)
*A61B 90/20* (2016.01)
(Continued)

(52) U.S. Cl.
CPC ................ *G06T 7/85* (2017.01); *A61B 90/20* (2016.02); *G02B 21/365* (2013.01); (Continued)

(58) Field of Classification Search
CPC ............. G06T 7/85; G06T 2207/10012; G06T 2207/10056; G06T 2207/30004;
(Continued)

(56) References Cited

U.S. PATENT DOCUMENTS 7,068,426 B2 6/2006 Bruehl et al.
7,599,531 B2 10/2009 Hauke et al.
(Continued)

FOREIGN PATENT DOCUMENTS

DE 10149750 A1 9/2002
DE 10225193 A1 1/2004
(Continued)

OTHER PUBLICATIONS

King et al., "Stereo Augmented Reality in the Surgical Microscope", Presence, vol. 9, No. 4, 360-368, Aug. 2000, Massachusetts Institute of Technology.

(Continued)

*Primary Examiner* — Susan E. Hodges
(74) *Attorney, Agent, or Firm* — Ewers IP Law PLLC; Falk Ewers

(57) ABSTRACT

A method for calibrating a stereoscopic medical microscope includes (a) capturing images of at least one three-dimensional calibration object using cameras of a stereo camera system of the medical microscope, (b) generating calibration data based on the captured images, the generated calibration data being stored for correction, (c) capturing further images of at least one two-dimensional calibration object with the cameras of the stereo camera system, and (d) generating further calibration data based on the captured further images, the further calibration data being stored for correction. In addition, a medical microscope arrangement is provided.

11 Claims, 2 Drawing Sheets

(51) Int. Cl.

| | |
|---|---|
| ***G02B 21/22*** | (2006.01) |
| ***G02B 21/36*** | (2006.01) |
| ***G06T 7/80*** | (2017.01) |
| ***H04N 23/67*** | (2023.01) |

(52) U.S. Cl.
CPC .... *H04N 13/239* (2018.05); *A61B 2560/0233* (2013.01); *G02B 21/22* (2013.01); *G06T 2207/10012* (2013.01); *G06T 2207/10056* (2013.01); *G06T 2207/30004* (2013.01); *H04N 23/675* (2023.01)

(58) Field of Classification Search
CPC .......... G06T 2207/30208; A61B 90/20; A61B 2560/0233; G02B 21/365; G02B 21/22; G02B 21/0012; H04N 13/239; H04N 23/675; H04N 13/246; G03B 15/14; G03B 35/08
USPC .......................................................... 348/47
See application file for complete search history.

(56) References Cited

U.S. PATENT DOCUMENTS

| | | | | |
|---|---|---|---|---|
| 7,766,481 | B2 | 8/2010 | Dick et al. | |
| 7,922,391 | B2 | 4/2011 | Essenreiter et al. | |
| 9,576,368 | B2 | 2/2017 | Fedorenko et al. | |
| 11,977,212 | B2 | 5/2024 | Raab et al. | |
| 2003/0012449 | A1* | 1/2003 | Usikov | G06T 5/94 382/145 |
| 2015/0346471 | A1 | 12/2015 | Schwarz et al. | |
| 2017/0102533 | A1* | 4/2017 | Wehe | H04N 23/81 |
| 2019/0107700 | A1 | 4/2019 | Lee et al. | |
| 2021/0157112 | A1 | 5/2021 | Raab et al. | |

FOREIGN PATENT DOCUMENTS

| | | | |
|---|---|---|---|
| DE | 102004020663 | A1 | 11/2005 |
| DE | 102004041115 | A1 | 3/2006 |
| DE | 102014210099 | B3 | 10/2015 |
| DE | 102018101162 | A1 | 7/2019 |
| DE | 102018125422 | A1 | 4/2020 |
| DE | 102019131646 | A1 | 5/2021 |
| EP | 2119397 | A1 | 11/2009 |
| EP | 2834789 | B1 | 3/2020 |
| EP | 3682424 | B1 | 2/2021 |
| WO | 20130103870 | A1 | 7/2013 |
| WO | 20190210322 | A1 | 10/2019 |

OTHER PUBLICATIONS

Wilson, "Modeling and Calibration of Automated Zoom Lenses", PhD thesis, The Robotics Institute, Carnegie Mellon University, Pittsburgh, Pennsylvania, USA, 1994.

International Search Report and Written Opinion dated May 3, 2023, of international application PCT/EP2023/051629, on which this application is based and English Language Translation thereof.

Office Action issued in German Patent Application No. DE 10 2022 200 821.9 (from which this application claims priority), dated Mar. 16, 2022 and English language machine translation thereof.

Garcia et al., "Calibration of a surgical microscope with automated zoom lenses using an active optical tracker", International journal of medical robotics and computer assisted surgery, Feb. 14, 2008, pp. 87-93, vol. 4, ISSN 1478-5951, MEM Research Centre, University of Bern, Switzerland.

Office Action dated Feb. 4, 2026, issued in European counterpart application No. 23702401.3 and English language translation thereof.

* cited by examiner

METHOD FOR CALIBRATING A STEREOSCOPIC MEDICAL MICROSCOPE, AND MEDICAL MICROSCOPE ARRANGEMENT

CROSS REFERENCE TO RELATED APPLICATIONS

This application is a continuation application of international patent application PCT/EP2023/051629, filed Jan. 24, 2023, designating the United States and claiming priority to German application 10 2022 200 821.9, filed Jan. 25, 2022, and the entire content of both applications is incorporated herein by reference.

TECHNICAL FIELD

The disclosure relates to a method for calibrating a stereoscopic medical microscope, and to a medical microscope arrangement.

BACKGROUND

The aim of digital visualization in surgery and microsurgery is to display to a surgeon, during an operation, an optimum three-dimensional image of the operation site and, if appropriate, an optimum three-dimensional superimposition of additionally generated information onto the field of view on the monitors of the medical microscope. In order to achieve this, captured camera images are processed by digital image processing with calibration data generated in a defined manner.

Methods for extrinsic and intrinsic calibration of cameras in connection with generation of distortion fields are known for example from Reg G. Willson, Modeling and Calibration of Automated Zoom Lenses, PhD thesis, The Robotics Institute, Carnegie Mellon University, Pittsburgh, Pennsylvania, USA, 1994. Furthermore, methods for calibrating a plurality of operating point settings (zoom and focus) with the aim of "Stereo Augmented Reality" are known from A. P. King et al., Stereo Augmented Reality in the Surgical Microscope, Presence, Vol. 9, No. 4, August 2000, 360-368, Massachusetts Institute of Technology.

Three-dimensional calibration objects are known from DE 10 2019 131 646 A1. The three-dimensional calibration objects have for example a transparent body and calibration marks embedded in the volume of the transparent body.

SUMMARY

It is an object of the disclosure to improve a method for calibrating a stereoscopic medical microscope and a medical microscope arrangement.

The object is achieved by a method for calibrating a stereoscopic medical microscope and a medical microscope arrangement as described herein.

A basic concept of the disclosure is to combine a three-dimensional calibration with a two-dimensional calibration and thereby to achieve overall an improved, in particular optimum, result of the calibration. This is done by image representations of at least one three-dimensional calibration object being captured with cameras of a stereo camera system of the medical microscope. In particular, each of the cameras of the stereo camera system captures at least one image representation. The image representations are captured in such a way that image representations of the two cameras of the stereo camera system for identical operating points of the medical microscope are combined with one another, that is to say, in particular, are assigned to one another or can be assigned to one another. Based on the captured image representations, calibration data are generated and stored for correction purposes. Furthermore, further image representations of at least one two-dimensional calibration object are captured with the cameras of the stereo camera system. These further image representations, too, are captured in such a way that the further image representations of the two cameras of the stereo camera system for identical operating points are combined with one another, that is to say are assigned or can be assigned to one another. In this case, the image representations and the further image representations are captured at the same operating points. Based on the captured further image representations, further calibration data are generated and stored for correction purposes. In this case, storing the calibration data includes storing the calibration data in a memory provided for this purpose, in order for said calibration data to be retrieved from said memory and applied as necessary. The stored calibration data and the stored further calibration data can be applied to image representations (and sequences of image representations, in particular videos) captured subsequently, in particular during an operation, such that these image representations can be corrected by the calibration data and further calibration data and can subsequently be acquired by a surgeon and/or further persons.

In particular, a method for calibrating a stereoscopic medical microscope is made available, including:

a) capturing image representations of at least one three-dimensional calibration object with cameras of a stereo camera system of the medical microscope,
b) generating calibration data based on the captured image representations, wherein the generated calibration data are stored for correction purposes,
c) capturing further image representations of at least one two-dimensional calibration object with the cameras of the stereo camera system,
d) generating further calibration data based on the captured further image representations, wherein the further calibration data are stored for correction purposes.

Furthermore, a medical microscope arrangement is provided, including a stereoscopic medical microscope having a stereo camera system including cameras, and storable calibration data and a data processing device, wherein the data processing device is configured to generate calibration data based on image representations of at least one three-dimensional calibration object that are captured with the cameras of the stereo camera system, and to store said calibration data for correction purposes, and to generate further calibration data based on further image representations of at least one two-dimensional calibration object that are captured with the cameras of the stereo camera system, and to store said further calibration data for correction purposes.

One advantage of the method and the medical microscope arrangement is that an overall calibration of the stereoscopic medical microscope can be achieved by way of a combination of a three-dimensional calibration and a two-dimensional calibration and associated two-dimensional and three-dimensional calibration objects. After the overall calibration data have been generated, image representations corrected with these calibration data can be provided to a surgeon and/or further persons. A superimposition for stereoscopic viewing of these respectively corrected image representations is improved by comparison with the uncorrected image representations, and such that a result conveying of information during an operation is also improved and disturbances owing to a deficient superimposition and/or owing to image aberrations and attendant adverse effects in the work sequence during an operation and fatigue phenomena can be reduced.

The calibration data and the further calibration data are generated by the captured image representations and captured further image representations being evaluated. In this case, features on the respective calibration objects are recognized and evaluated. Since the calibration objects have known properties, the calibration data and the further calibration data can be generated, in particular determined, based on the known properties and the evaluated captured image representations and further image representations. In particular, the respective features and their properties, in particular a pose (position and orientation), geometric arrangement, shape, color, brightness, etc., are known, and can therefore be recognized in the image representations and further image representations. By way of a comparison of the known target properties of the respective features in the image representations and further image representations and the actual properties, the calibration data and the further calibration data can be determined in a manner known per se with known calibration methods. The evaluation is effected with the data processing device. In this case, computer vision, pattern recognition and/or machine learning methods known per se can be used.

A medical microscope is a surgical microscope. However, a medical microscope may also be a microscope used for medical examinations and/or for diagnostic purposes, for example in the field of ophthalmology or in other fields. A medical microscope arrangement is a surgical microscope arrangement.

Calibration data and further calibration data can in principle be identical or different in nature and concern different properties and/or effects and/or disturbances and/or devices of the medical microscope. The differentiation between calibration data and further calibration data has been chosen for linguistic differentiation.

A two-dimensional calibration object can have shapes and patterns known per se, for example a two-dimensional checkered pattern, line markings, cross hairs and the like. A three-dimensional calibration object has three-dimensional structures. A three-dimensional calibration object can have structures which, in relation to an optical axis of the imaging system of the medical microscope, are arranged in a plurality of planes perpendicular to said axis and can be captured for example by irradiation and/or by a defined intrinsic illumination with the medical microscope or with the cameras. For example, these can be high-contrast markings which are arranged in two mutually perpendicular planes in order to create depth information in relation to the optical axis (cf., e.g., FIG. 2 in King et al.). Three-dimensional calibration objects are also described for example in DE 10 2019 131 646 A1. A three-dimensional calibration object therefore has for example a transparent body and calibration marks embedded in the volume of the transparent body. In one of the embodiments described in DE 10 2019 131 646 A1, a three-dimensional calibration object is essentially a cubic 3D calibration body constructed from transparent layers. The 3D calibration body is constructed from stacked light guides. The light guides are formed by mutually alternating transparent layers, the layers having a higher refractive index than layers arranged therebetween. With selectively switchable light sources, light is coupled into the layers in such a way that it is subjected to total internal reflection at interfaces between the layers. There is light propagation, i.e., a propagation of the electromagnetic waves of the light, only within the respective light guides on account of the total internal reflection at the interfaces between the layers. In order to be able to represent calibration marks in the light guides of the 3D calibration body, thin films are applied at certain distances on the layers. Here, the refractive index of these films is chosen in such a way that the total internal reflection is suppressed at these points such that there is light propagation into the layers with a low refractive index. If light is then coupled into one of the light guides, the light is output coupled from the light guide at those points at which the films have been applied such that luminous points arise in the volume of the transparent body constructed from the layers, said luminous points serving as calibration marks. The luminous points arise at different depths of the transparent body depending on which light source is activated.

It can also be provided that at least one two-dimensional calibration object and at least one three-dimensional calibration object are combined to form a combined calibration object. The sequence of the method is then the same, in principle.

Parts of the medical microscope arrangement, in particular the data processing device, can be configured, either individually or together, as a combination of hardware and software, for example as program code that is executed on a microcontroller or microprocessor. By way of example, the data processing device can include a computing device in the form of a microprocessor or microcontroller and a memory. However, it can also be provided that parts are configured, either individually or together, as an application-specific integrated circuit (ASIC) and/or a field-programmable gate array (FPGA). The data processing device can also be part of the medical microscope. However, in principle the data processing device can also be formed separately from the medical microscope, for example as a desktop, laptop or tablet computer, or else as a cloud-based solution.

In one exemplary embodiment, it is provided that step a) and/or step c) are/is carried out at different operating points of the medical microscope, wherein the calibration data in step b) and/or the further calibration data in step d) are generated for each of the different operating points. As a result, calibration data can be generated over a larger, in particular over an entire, working and/or operating range of the medical microscope. In this case, an operating point includes in particular one or more of the following parameters: a pose (position and/or orientation) of the camera(s) and/or a magnification (zoom) and/or a working distance (focus or a position of the focusing lens) and/or a position of a stop and/or a value of a stop opening (aperture stop) and/or a presence of a drape lens at the microscope (yes/no). In this case, it can be provided that calibration data and further calibration data for operating points for which no image representations and/or further image representations have been captured are generated from calibration data and/or further calibration data of adjacent operating points, in particular by interpolation and/or extrapolation. It can also be provided that calibration data for such operating points are estimated with the aid of a function which is fitted to the calibration data generated based on operating points being measured.

In one exemplary embodiment, it is provided that the calibration data generated in step b) and/or the further calibration data generated in step d) for correction purposes are at least partly applied to the captured image representations and/or the captured further image representations, wherein step b) is carried out and/or repeated for the corrected image representations and/or step d) is carried out and/or repeated for the corrected further image representations. As a result, the calibration data and/or the further calibration data can be optimized step by step since already generated calibration data and/or further calibration data are applied to the captured image representations and/or the captured further image representations. In particular, a plurality of different effects which lead to disturbances between the image representations and/or the further image representations and which can influence one another can be taken into account as a result. In this regard, for example, a distortion aberration in an image representation captured with a left camera of the stereo camera system can influence an offset between the captured image representations of the left camera and a right camera of the stereo camera system, and vice versa. If the distortion aberration is corrected prior to determining the offset, then the effect of the distortion aberration when determining the offset can be minimized or even eliminated.

In particular, it is provided that the calibration data generated in step b) for correction purposes are first at least partly applied to the captured further image representations before step d) is performed. As a result, step d) can be carried out with captured further image representations already corrected by the calibration data. In particular, an effect of mutually influencing disturbances can be reduced as a result.

In one exemplary embodiment, it is provided that the correction and steps c) and d) are repeated until at least one predefined optimization criterion is satisfied. As a result, the further calibration data can be improved step by step. The at least one predefined optimization criterion is for example a predefined maximum value (e.g., +/−1 pixel) for an (x-/y-) offset between the captured further image representations of the two cameras of the stereo camera system and/or a predefined maximum value (e.g. +/−0.001° in relation to an image midpoint) for a rotation between the captured further image representations of the two cameras of the stereo camera system.

If the steps of the method are performed in the order c), d), a), b), then it is likewise possible for the image representations captured in step a) to be corrected with the further calibration data generated in step d) before step b) is performed. In this case, in principle, the procedure is analogous to the procedure described above.

In one exemplary embodiment, it is provided that the generated calibration data are checked by at least partial application to the captured image representations and/or the captured further image representations and assessment of a result of the application, wherein steps a) to d) are at least partly repeated if an assessment result does not satisfy at least one predefined criterion. An assessment result can include for example values for deviations which are determined for selected variables. The selected variables can include for example one or more of the following variables: an offset, a rotation, a difference in brightness, a distortion, etc. A predefined criterion includes for example predefined limit values for the respective assessment results, that is to say maximum permissible values for the respective deviations. It can furthermore be provided that individual assessment results for the selected variables are aggregated to form a single assessment result and are compared with the at least one criterion (e.g., with a maximum value for an aggregated deviation).

In one exemplary embodiment, it is provided that step b) and/or step d) include(s) one or more of the following measures: determining extrinsic calibration data, determining intrinsic calibration data, determining distortion correction field data, determining edge decrease correction data, and determining chromatic displacement field correction data.

For the extrinsic calibration data and/or intrinsic calibration data, in particular, camera projection matrices are determined with methods known per se. Methods for extrinsic and intrinsic calibration of cameras are known for example from one of the documents cited in the introduction (Reg G. Willson, 1994).

In order to determine the distortion correction field data, with a suitable calibration object, in the simplest case for example with a calibration object with a plurality of mutually perpendicular straight lines within a plane that is perpendicular to the optical axis of the medical microscope, or with a checkered pattern, in particular a distortion of the captured image representations is determined and a dedistortion field is determined based on the determined distortion, and the distortion correction field data are then derived from said dedistortion field. In order to determine the distortion correction field data in an improved manner, in particular three-dimensional structures of the three-dimensional calibration object are captured and evaluated. This is described in King et al., for example.

In order to determine the edge decrease correction data, in particular (camera) vignetting in the captured image representations is determined, which is corrected by the edge decrease correction data in such a way that brightness values in the captured image representations do not decrease in the direction of the edge of the captured image representations. In particular, for this purpose, image representations of a homogeneously self-luminous three-dimensional calibration object are captured for different operating points (working distance, zoom, etc.). In the context of an evaluation carried out in step b), a brightness profile in the captured image representations is determined and, based on the determined brightness profile, the edge decrease correction data are determined in such a way that captured image representations of the homogeneously self-luminous three-dimensional calibration object that are corrected with the edge decrease correction data have a constant, that is to say homogeneous, brightness across the entire calibration object.

With the chromatic displacement field correction data, in particular, a lateral chromatic aberration is intended to be corrected, that is to say that, in particular, a color fringe that is visible at edges is intended to be corrected. In order to determine the chromatic displacement field correction data, in particular, a color channel-dependent evaluation of the captured image representations of a three-dimensional calibration object is effected. In particular, in a color channel-dependent manner, an offset (e.g. x-/y-offset) is determined and for each color channel an offset field is determined for the captured image representations. As a result of the chromatic aberration, for example, an edge with a color fringe in each color channel has a slightly different position in the captured image representation. The correction field respectively generated from the offset field then specifies how the captured image representation must be displaced in the respective color channel in order that the image representations of all the color channels lie one above another with pixel accuracy and the color fringe disappears as a result. The correction fields of all the color channels then yield the displacement field correction data.

In one exemplary embodiment, it is provided that step b) includes determining the respective focus position of the cameras of the stereo camera system and setting the respective focus position. Setting the focus position is effected in particular based on the focus positions respectively determined for the cameras of the stereo camera system from the image representations. The aim of the determining and setting is for the cameras always to have the same (actual) focus position at every operating point. Setting the focus position is effected by a technician, for example, to whom the values for the focus positions determined based on the captured image representations are displayed on a display device of the medical microscope. The technician then adjusts the focus positions in such a way that the (actual) focus positions are always the same at the different operating points for both cameras of the stereo camera system. In principle, however, automated adjustment can also be effected, for example with an actuator system of the medical microscope that is configured for this purpose.

In one exemplary embodiment, it is provided that step d) includes determining an offset between the captured further image representations of the cameras of the stereo camera system and determining offset correction data and/or determining a rotation between the captured further image representations of the cameras of the stereo camera system and determining rotation correction data. An offset (e.g., x-/y-offset) and/or a rotation between the captured further image representations of the cameras are/is determined with reference to a respective image center of the captured further image representations.

In one exemplary embodiment, it is provided that different operating points of a movable lens system of the stereoscopic medical microscope are selected when capturing at least some of the image representations in the context of step a) or c), wherein an offset value is determined for each of the operating points of the movable lens system in the context of step b) or d), wherein the calibration data and/or further calibration data are generated taking account of the offset values respectively determined. As a result, an offset across different operating points of the movable lens system that is caused by the movable lens system can also be corrected. An offset value denotes an (x-/y-) offset value of pixels in image representations captured by the two cameras. By virtue of different operating points being selected, a position of the lenses within the lens system changes. If an optical axis of the lens system changes in the process, for example as a result of tolerances and inaccuracies in the mechanism and in an actuator system used, then imaging aberrations may occur which can lead to an offset between the captured image representations and/or captured further image representations of the two cameras of the stereo camera system. Such an offset can then be corrected at each operating point with the generated calibration data and/or further calibration data. For operating points for which no offset values were determined, calibration data and/or further calibration data can be generated by interpolation or extrapolation.

In one exemplary embodiment, it is provided that at least one additional image representation of a homogeneously reflecting and/or reflective calibration object is furthermore captured with the stereo camera system, wherein illumination correction data for correcting an illumination geometry of at least one light source of the medical microscope are generated based on the captured at least one additional image representation and are taken into account when generating the calibration data and/or the further calibration data. As a result, an inhomogeneous illumination geometry of the at least one light source can also be corrected. The illumination correction data can be included by the calibration data or further calibration data. The homogeneously reflecting and/or reflective calibration object can also be part of the at least one three-dimensional or of the at least one two-dimensional calibration object.

Further features relating to the configuration of the medical microscope arrangement are evident from the description of configurations of the method. Here, the advantages of the medical microscope arrangement are in each case the same as in the configurations of the method.

BRIEF DESCRIPTION OF THE DRAWINGS

The disclosure will now be described with reference to the drawings wherein.

DESCRIPTION OF EXEMPLARY EMBODIMENTS

Figure 1:
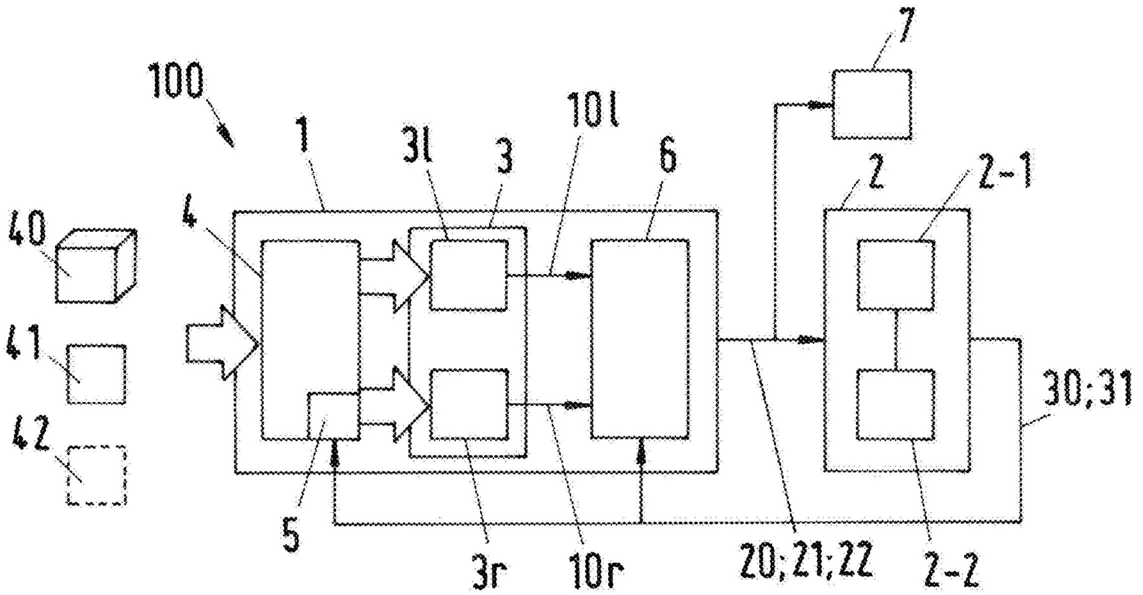
FIG. 1 shows a schematic illustration of the medical microscope arrangement according to an exemplary embodiment of the disclosure.

FIG. 1 shows a schematic illustration of a medical microscope arrangement 100 according to an exemplary embodiment of the disclosure. The medical microscope arrangement 100 includes a stereoscopic medical microscope 1, for example a surgical microscope, and a data processing device 2. The method described in this disclosure is explained below based on the medical microscope arrangement 100.

The stereoscopic medical microscope 1 includes a stereo camera system 3, which includes a left camera **3*l* and a right camera 3*r*. The cameras 3*l*, 3*r* capture a capture region imaged by way of a stereoscopic imaging optical unit 4 (only illustrated schematically) of the medical microscope 1. In order to correct errors in an adjustment for the imaging optical unit 4 calibration data 30 and further calibration data 31, for example for an actuator system 5 configured to change properties of the imaging optical unit 4**, can be stored.

Furthermore, the medical microscope 1 includes a signal processing device 6, which processes a raw signal **10*l* provided by an image sensor of the left camera 3*l* and a raw signal 10*r* provided by an image sensor of the right camera 10*r* and which generates and provides image representations 20 and further image representations 21 from the raw signals 10*l*, 10*r*. By way of example, the image representations 20, 21 can be displayed on at least one display device 7, for example one or more monitors or a head-mounted display (HMD), which can also be part of the medical microscope 1. The signal processing can include a pixel-dependent modification of a brightness and/or a generation of an offset and/or a rotation about an image midpoint (or any other point), and further manipulations (filtering, color correction, etc.). Calibration data 30, 31 for correcting the raw signals 10*l*, 10*r* can be stored in the signal processing device 6**.

Provision can also be made for the calibration data 30, 31 to be stored only in the image processing device 6.

The data processing device 2 includes a computing device 2-1, for example a microprocessor or microcontroller, and a memory 2-2. The data processing device 2 can also be part of the medical microscope 1.

The data processing device 2 is configured to generate the calibration data 30 based on image representations 20 of at least one three-dimensional calibration object 40 that are captured with the cameras **3*l*, 3*r* of the stereo camera system 3, and to store said calibration data for correction purposes. Furthermore, the data processing device 2 is configured to generate the further calibration data 31 based on further image representations 21 of at least one two-dimensional calibration object 41 that are captured with the cameras 3*l*, 3*r* of the stereo camera system 3**, and to store said further calibration data for correction purposes.

In particular, with the medical microscope arrangement 100, a method for calibrating the stereoscopic medical microscope 1 is performed, including:

a) capturing image representations 20 of the at least one three-dimensional calibration object 40 with the cameras **3*l*, 3*r* of the stereo camera system 3 of the medical microscope 1, b) generating the calibration data 30 based on the captured image representations 20, wherein the generated calibration data 30 are stored for correction purposes, c) capturing further image representations 21 of the at least one two-dimensional calibration object 41 with the cameras 3*l*, 3*r* of the stereo camera system 3, and d) generating the further calibration data 31 based on the captured further image representations 21, wherein the further calibration data 31** are stored for correction purposes.

It can be provided that step a) and/or step c) are/is carried out at different operating points of the medical microscope 1, wherein the calibration data 30 in step b) and/or the further calibration data 31 in step d) are generated for each of the different operating points. In this case, an operating point can include in particular parameters for the following settings: a pose (position and/or orientation) of the camera(s) and/or a magnification (zoom), a working distance (focus or a position of the focusing lens), a position of a stop, a value of a stop opening (aperture stop), a presence of a drape lens (yes/no), etc.

In this case, the different operating points can be set both manually and in an automated manner. In the case of manual setting, provision can be made for parameters of the medical microscope 1 to be displayed to a technician, for example, such that the latter can set the parameters for each operating point. In the case of automated setting, the data processing device 2 can be configured to generate suitable control parameters and to feed them to the medical microscope 1, in particular to the actuator system 5, for the purpose of setting the different operating points.

It can be provided that the calibration data 30 generated in step b) and/or the further calibration data 31 generated in step d) for correction purposes are at least partly applied to the captured image representations 20 and/or the captured further image representations 21, wherein step b) is carried out and/or repeated for the corrected image representations 20 and/or step d) is carried out and/or repeated for the corrected further image representations 21. In this case, the correction can be effected both in the signal processing device 6 and in the data processing device 2.

It can be provided that the correction and steps c) and d) are repeated until at least one predefined optimization criterion is satisfied. For this purpose the further calibration data 31 are stored before each repetition in the medical microscope 1, in particular in the image processing device 6. Steps c) and d) are then carried out again with changed further calibration data 31. As a result, a calibration of the medical microscope 1 can be progressively and iteratively improved.

In particular, it is provided that step b) includes one or more of the following measures: determining extrinsic calibration data, determining intrinsic calibration data, determining distortion correction field data, determining edge decrease correction data, determining chromatic displacement field correction data. The generated calibration data 30 then include the extrinsic calibration data and/or intrinsic calibration data and/or distortion correction field data and/or edge decrease correction data and/or chromatic displacement field correction data.

It can be provided that step b) includes determining the respective focus position of the cameras **3*l*, 3*r* of the stereo camera system 3 and setting the respective focus position. The (actual) focus position can be set or adjusted based on a value respectively determined for the focus position. This can be done, in principle, both manually by a technician and in an automated manner and/or in a motorized manner with the actuator system 5. The aim is for the focus position of both cameras 3*l*, 3*r*** always to be the same at different operating points.

It can be provided that step d) includes determining an offset between the captured further image representations 21 of the cameras **3*l*, 3*r* of the stereo camera system 3 and determining offset correction data and/or determining a rotation between the captured further image representations 21 of the cameras 3*l*, 3*r* of the stereo camera system 3 and determining rotation correction data. The generated further calibration data 31** then include the offset correction data and/or the rotation correction data.

It can be provided that different operating points of a movable lens system of the stereoscopic medical microscope 1 are selected when capturing at least some of the image representations 20, 21 in the context of step a) or c), wherein an offset value is determined for each of the operating points of the movable lens system in the context of step b) or d), wherein the calibration data 30 and/or the further calibration data 31 are generated taking account of the offset values respectively determined.

It can be provided that at least one additional image representation 22 of a homogeneously reflecting and/or reflective calibration object 42 is furthermore captured with the stereo camera system 3, wherein illumination correction data for correcting an illumination geometry of at least one light source (not shown) of the medical microscope 1 are generated based on the captured at least one additional image representation 22 and are taken into account when generating the calibration data 30 and/or the further calibration data 31. The illumination correction data are determined for this with the data processing device 2. For this purpose, the data processing device 2 determines a brightness profile for different operating points, in the captured at least one additional image representation 22. Since a brightness should be constant in the captured at least one additional image representation 22, the illumination correction data can be generated based on the respective brightness profile, in particular can be determined from the brightness profile. For correction purposes, the illumination correction data are stored as calibration data 30, 31 in the signal processing device 6 during ongoing operation. The signal processing device 6 then applies the illumination correction data to the raw signals **10*l*, 10*r***.

Capturing the at least one additional image representation 22 of the homogeneously reflecting and/or reflective calibration object 42 and generating the illumination correction data take place in particular after steps a) to d). In particular, a correction based on the edge decrease correction data (for the correction of camera vignetting) may have already been carried out before the brightness profile and the illumination correction data are determined. However, it can also be provided that the homogeneously reflecting and/or reflective calibration object 42 is part of the two-dimensional calibration object 41. Capturing the at least one additional image representation 22 of the homogeneously reflecting and/or reflective calibration object 42 can then also be effected simultaneously with other steps, for example with step c).

Figure 2A:
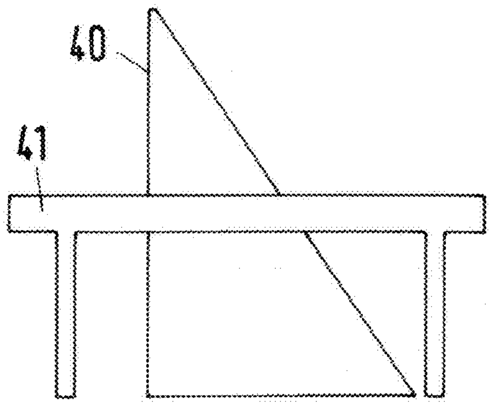
FIG. 2A shows schematic illustrations of a three-dimensional calibration object and of a two-dimensional calibration object in a side view.
Figure 2B:
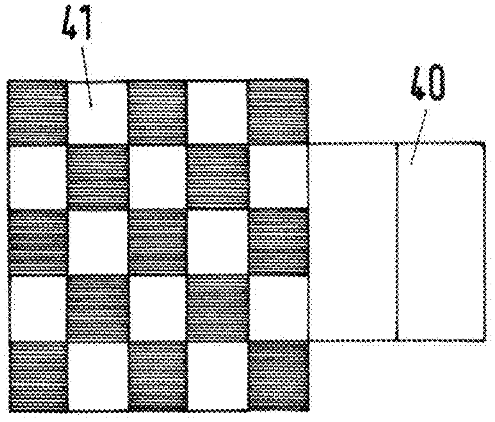
FIG. 2B shows schematic illustrations of the three-dimensional calibration object and of the two-dimensional calibration object in a plan view.

FIGS. 2A and 2B show schematic illustrations of exemplary embodiments of the three-dimensional calibration object 40 and of the two-dimensional calibration object 41. In this case, FIG. 2A shows a side view and FIG. 2B shows a plan view corresponding to a view of how the medical microscope 1 would capture the calibration objects 40, 41 with the cameras 3*l*, 3*r*. The three-dimensional calibration object 40 has a triangular shape with an inclined face (it may therefore also be referred to as an "oblique target"), such that different distances (e.g., z-direction) can be captured simultaneously. The two-dimensional calibration object 41 has a checkered pattern on a top side. In particular, an offset (e.g. x-/y-direction) and a rotation between the (further) image representations 20, 21 captured by the cameras 3*l*, 3*r* of the stereo camera system 3 can be determined with the aid of the checkered pattern. In principle, the two-dimensional calibration object 41 can additionally or alternatively also have other suitable structures, such as, for example, rectangles, lines, and/or other suitable two-dimensional shapes, etc.

In the example shown, the calibration objects 40, 41 are represented jointly as a combined object. However, the calibration objects 40, 41 can also be formed separately from one another and/or used separately from one another.

In particular, it can also be provided that the three-dimensional calibration object 40 is configured in accordance with one of the embodiments described in DE 10 2019 131 646 A1, in particular in accordance with one embodiment in FIG. 5 or FIG. 6 shown therein.

Figure 3:
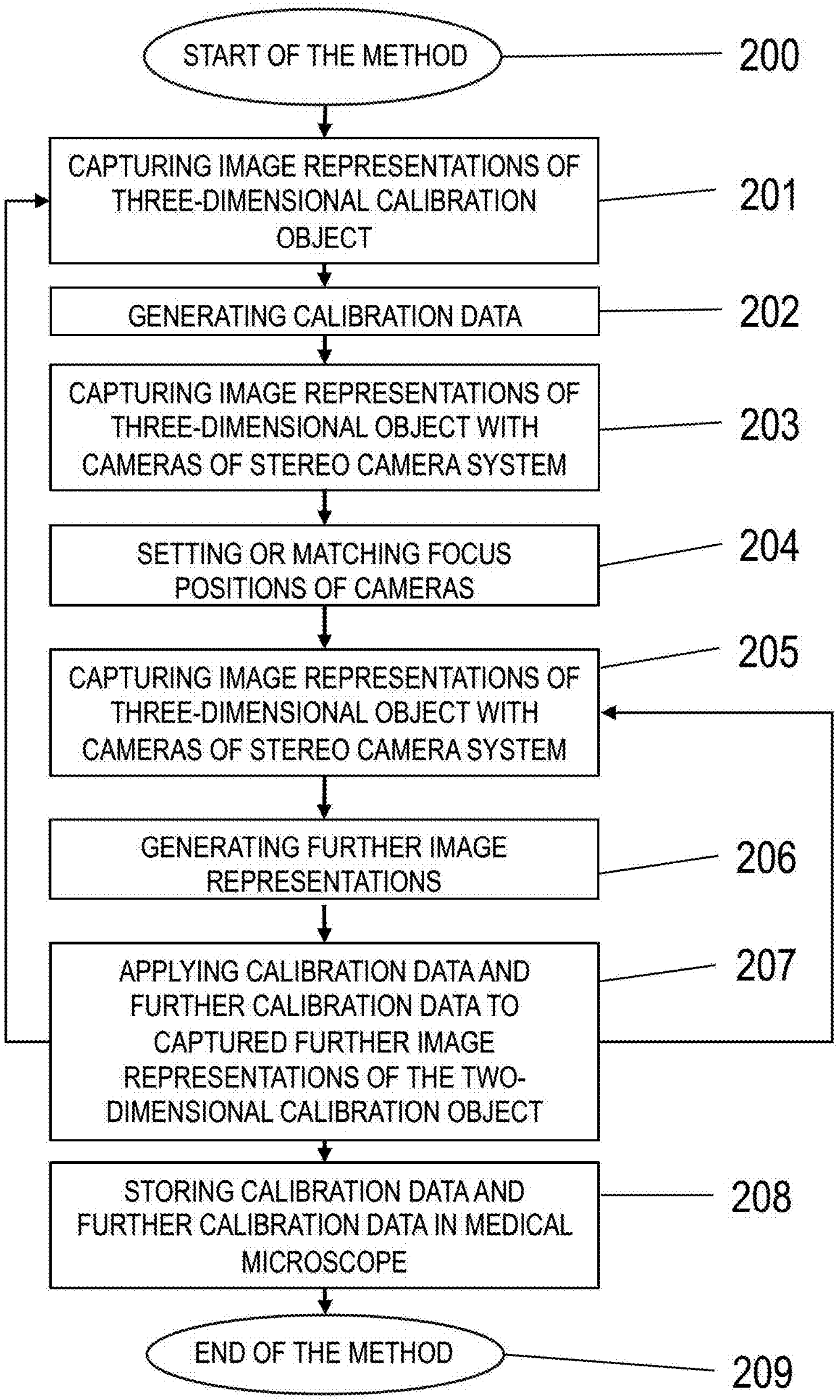
FIG. 3 shows a schematic flow diagram of the method for calibrating a stereoscopic medical microscope according to an exemplary embodiment of the disclosure.

FIG. 3 shows a schematic flow diagram of one exemplary embodiment of the method for calibrating a stereoscopic medical microscope. The method is performed for example with a medical microscope arrangement such as is shown in FIG. 1.

After the start 200 of the method, which can be initiated by a technician, for example, in a method step 201, image representations of at least one three-dimensional calibration object are captured with cameras of a stereo camera system of the medical microscope. Prior to the capturing, for this purpose a (at least one) three-dimensional calibration object is arranged in the capture region of the medical microscope. Provision is made for method step 201 to be carried out for different operating points of the medical microscope.

In a method step 202, with a data processing device, calibration data are generated based on the captured image representations, in particular are determined based on the captured image representations. The generated calibration data are stored for correction purposes in a memory—provided for this—of the medical microscope, for example in a memory of a signal processing device and/or a control device and/or an actuator system of the medical microscope. Generating, in particular determining, the calibration data is effected for each of the different operating points. The generated or determined, calibration data include in particular camera projection matrices (extrinsic calibration data and/or intrinsic calibration data) and/or distortion correction field data and/or edge decrease correction data and/or chromatic displacement field correction data.

Depending on the nature of the calibration data to be determined, provision can be made for using different three-dimensional calibration objects in each case. For each of the three-dimensional calibration objects, in method step 201, image representations are then captured at different operating points.

In a method step 203, image representations of at least one three-dimensional calibration object are captured with the cameras of the stereo camera system. This is done with the aid of the three-dimensional calibration object 40 ("oblique target") shown in FIG. 2A. The inclined face makes it possible to assess a blurring profile in a captured image representation along the optical axis (z-direction), such that a respective focus position of the cameras can be determined. The capturing can be effected in particular for different operating points, in particular at different working distances with respect to the three-dimensional calibration object. Respective focus positions of the cameras of the stereo camera system are determined based on the captured image representations.

In a method step 204, the focus positions of the cameras are set or matched to one another based on the determined values. This is done manually by a technician. In particular, this is done in such a way that the focus positions are always the same at the different operating points (in particular working distances) for both cameras.

In a method step 205, further image representations of at least one two-dimensional calibration object are captured with the cameras of the stereo camera system.

In a method step 206, further calibration data are generated or determined, based on the captured further image representations. It is provided that an offset (x-/y-offset) between the captured further image representations of the cameras of the stereo camera system and offset correction data and also a rotation between the captured further image representations of the cameras of the stereo camera system and rotation correction data are determined. The generated or determined further calibration data are stored for correction purposes in a memory—provided for this—of the medical microscope, for example in a memory of a signal processing device and/or a control device and/or an actuator system of the medical microscope.

Depending on the nature of the calibration data to be determined, provision can be made for using different two-dimensional calibration objects in each case. For each of the two-dimensional calibration objects, in method step 205, image representations are then captured at different operating points.

In a method step 207, the calibration data and the further calibration data are applied to the captured further image representations of the two-dimensional calibration object; and the captured further image representations are corrected thereby. This can be done for example with the signal processing device 6 (FIG. 1) by virtue of the latter correcting the raw signals 10*l*, 10*r* with the stored calibration data and the stored further calibration data and providing the results, that is to say the image representations corrected in this way.

Provision can be made for method steps 205, 206, and 207 subsequently to be repeated. In particular, provision is made here for method steps 205, 206, and 207 to be repeated until at least one predefined optimization criterion is satisfied. In this case, predefined optimization criteria can be for example maximum values for an offset and/or a rotation (e.g., +/−1 pixel and/or)+/−0.001° between the image representations of the two cameras of the stereo camera system.

In method step 207, it can be provided that the generated calibration data are checked by at least partial application to the captured image representations and/or the captured further image representations and assessment of a result of the application, wherein method steps 201 to 207 are at least partly repeated if an assessment result does not satisfy at least one predefined criterion. The at least one predefined criterion can include for example maximum values for an offset and/or a rotation between the image representations of the two cameras of the stereo camera system, respective maximum values for a distortion of the cameras and/or respective maximum values for an edge decrease in brightness (camera vignetting), etc.

Once the calibration data have been optimized and/or checked, then the calibration data and the further calibration data are stored in the medical microscope for application in the field in a method step 208. The method is then ended 209.

LIST OF REFERENCE NUMERALS

1 Medical microscope
2 Data processing device
2-1 Computing device
2-2 Memory
3 Stereo camera system
**3*l*** Left camera
**3*r*** Right camera
4 Imaging optical unit
5 Actuator system
6 Signal processing device
7 Display device
**10*l*** Raw signal (left camera)
**10*r*** Raw signal (right camera)
20 Image representation
21 Further image representation
22 Additional image representation
30 Calibration data
31 Further calibration data
40 Three-dimensional calibration object
41 Two-dimensional calibration object
42 Homogeneously reflecting and/or reflective calibration object
100 Medical microscope arrangement
200 to 209 Method steps of the method

What is claimed is:

1. A method for calibrating a stereoscopic medical microscope, the method comprising:

(a) capturing image representations of at least one three-dimensional calibration object with cameras of a stereo camera system of the medical microscope;

(b) generating calibration data based on the captured image representations, wherein the generated calibration data are stored for correction purposes;

(c) capturing further image representations of the at least one two-dimensional calibration object with the cameras of the stereo camera system; and (d) generating further calibration data based on the captured further image representations, wherein the further calibration data are stored for the correction purposes, wherein at least one of:

(c1) the calibration data generated in step (b) for the correction purposes are applied at least partially to the further image representations captured in step (c), and step (d) is performed and/or repeated based on the further image representations corrected in step (c1), and (a1) the further calibration data generated in step (d) for the correction purposes are applied at least partially to the image representations captured in step (a), and step (b) is performed and/or repeated based on the image representations corrected in step (a1), wherein the stored calibration data and further calibration data are applied to subsequently captured image representations, such that the subsequently captured image representations are corrected by the calibration data and the further calibration data, and wherein corrected image representations are provided.

2. The method as claimed in claim 1, wherein at least one of step (a) and step (c) are/is carried out at different operating points of the medical microscope, and wherein the at least one of the calibration data in step (b) and the further calibration data in step (d) are generated for each of the different operating points.

3. The method as claimed in claim 1, wherein at least one of the calibration data generated in step (b) and the further calibration data generated in step (d) for correction purposes are at least partly applied to at least one of the captured image representations and the captured further image representations, and wherein at least one of step (b) is carried out and repeated for the image representations, and step (d) is carried out and repeated for the corrected further image representations.

4. The method as claimed in claim 3, wherein the correction and steps (c) and (d) are repeated until at least one predefined optimization criterion is satisfied.

5. The method as claimed in claim 1, wherein the generated calibration data are checked by at least one of at least partial application to the captured image representations and the captured further image representations and assessment of a result of the application, and wherein steps (a) to (d) are at least partly repeated when an assessment result does not satisfy at least one predefined criterion.

6. The method as claimed in claim 1, wherein at least one of step (b) and step (d) include(s) one or more of the following measures:

determining extrinsic calibration data,
determining intrinsic calibration data,
determining distortion correction field data,
determining edge decrease correction data, and
determining chromatic displacement field correction data.

7. The method as claimed in claim 1, wherein step (b) includes determining a respective focus position of the cameras of the stereo camera system and setting the respective focus position.

8. The method as claimed in claim 1, wherein step (d) includes at least one of determining an offset between the captured further image representations of the cameras of the stereo camera system and determining offset correction data and determining a rotation between the captured further image representations of the cameras of the stereo camera system and determining rotation correction data.

9. The method as claimed in claim 1, wherein different operating points of a movable lens system of the stereoscopic medical microscope are selected when capturing at least some of the image representations in step (a) or (c), wherein an offset value is determined for each of the operating points of the movable lens system in step (b) or (d), and wherein at least one of the calibration data and further calibration data are generated taking account of the offset values respectively determined.

10. The method as claimed in claim 1, wherein at least one additional image representation of at least one of a homogeneously reflecting and reflective calibration object is furthermore captured with the stereo camera system, and wherein illumination correction data for correcting an illumination geometry of at least one light source of the medical microscope are generated based on the at least one additional image representation and are taken into account when generating at least one of the calibration data and the further calibration data.

11. A medical microscope arrangement, comprising:

a stereoscopic medical microscope having a stereo camera system including cameras, storable calibration data, and a data processing device, wherein the data processing device is configured to:

(a) generate calibration data based on image representations of at least one three-dimensional calibration object that are captured with the cameras of the stereo camera system, and store the calibration data for correction purposes, and (b) generate further calibration data based on further image representations of at least one two-dimensional calibration object that are captured with the cameras of the stereo camera system, and store said further calibration data for the correction purposes, wherein at least one of:

(c) the calibration data generated in step (a) for the correction purposes are applied at least partially to the further image representations captured with the cameras of the stereo camera system, and step (b) is performed and/or repeated based on the further image representations corrected in step (c), and (d) the further calibration data generated in step (b) for the correction purposes are applied at least partially to the image representations captured with the cameras of the stereo camera system, wherein step (a) is performed and/or repeated based on the image representations corrected in step (d), wherein the stored calibration data and further calibration data are applied to subsequently captured image representations, such that the subsequently captured image representations are corrected by the calibration data and the further calibration data, and wherein corrected image representations are provided.

* * * * *